United States Patent [19]
Philipp

[11] Patent Number: 5,235,261
[45] Date of Patent: Aug. 10, 1993

[54] DC POWERED SURGICAL HANDPIECE HAVING A MOTOR CONTROL CIRCUIT

[75] Inventor: Christopher D. Philipp, Portage, Mich.

[73] Assignee: Stryker Corporation, Kalamazoo, Mich.

[21] Appl. No.: 869,627

[22] Filed: Apr. 16, 1992

Related U.S. Application Data

[62] Division of Ser. No. 722,017, Jun. 27, 1991, Pat. No. 5,136,220.

[51] Int. Cl.⁵ .............................................. H02P 7/14
[52] U.S. Cl. ........................................ 318/504; 388/937
[58] Field of Search ........................ 318/17, 254, 504;
388/937; 323/220, 222, 223, 224, 225, 226, 229, 231, 232, 304, 311; 363/123, 124

[56] References Cited

U.S. PATENT DOCUMENTS

| | | | |
|---|---|---|---|
| 4,347,474 | 8/1982 | Brooks et al. | 323/224 |
| 4,354,223 | 10/1982 | Turnbull | 363/124 |
| 4,429,269 | 1/1984 | Brown | 323/301 |
| 4,618,812 | 10/1986 | Kawakami | 323/224 |
| 4,749,923 | 6/1988 | Chieng | 318/269 |
| 4,752,724 | 6/1988 | Radziwill et al. | 318/254 |
| 4,843,300 | 6/1989 | Alderman | 323/224 |
| 4,879,498 | 11/1989 | Shinohara et al. | 318/254 |
| 4,958,948 | 9/1990 | Seima et al. | 388/812 |

OTHER PUBLICATIONS

Drawing A (Stryker Part No. SK-3864, Command Console).
Drawing B (Stryker Brushless Decoder, EPLD No. EP320).
Drawing C (Stryker Part No. SK-6963, OP90 II Speed Control).
Stryker brochure entitled "New OrthoPower 90 cordless instruments—The Power and The Freedom" (7 pages).

*Primary Examiner*—Bentsu Ro
*Attorney, Agent, or Firm*—Flynn, Thiel, Boutell & Tanis

[57] ABSTRACT

A compact surgical handpiece comprises a motor energizable for moving a tool member, electric energy supply actuable for energizing the motor and a manually actuable trigger actuable to control motor operation. A motor control circuit interconnects the motor electric energy supply and trigger for running and braking the motor in response to actuation and release of the trigger. The control circuit includes a compact regulated voltage supply, a motor overcurrent limiting feature and a motor braking feature which is effective even if the operator fails to fully disconnect the electrical supply to the motor upon releasing the trigger.

12 Claims, 3 Drawing Sheets

DC POWERED SURGICAL HANDPIECE HAVING A MOTOR CONTROL CIRCUIT

This is a division of Ser. No. 07/722,017, filed Jun. 27, 1991, now U.S. Pat. No. 5,136,220.

FIELD OF THE INVENTION

This invention relates to a DC powered surgical handpiece having a motor control circuit.

BACKGROUND OF THE INVENTION

DC powered surgical handpieces have been commercially available for a number of years. These include battery operated surgical handpieces in the form of a self-contained handpiece incorporating a rechargeable battery. The assignee of the present invention has produced battery carrying handpieces of this type, including drills, reamers and saws, such as sagittal and reciprocating saws.

The present applicant has found that it is possible to improve over prior DC powered handpieces, particularly battery handpieces, in several respects.

For example, the present applicant has found that it is important to provide a control which is not only capable of providing the usual forward/reverse and variable speed control functions, but which can also be made physically compact so as to take minimal space in the handpiece and be conveniently located in the handpiece while not interfering with the balance of the handpiece and the ability of the handpiece to fit comfortably in the hand of prospective users.

Applicant has found it possible to achieve a desired motor power capability while limiting the peak current draw on the battery and thereby avoiding possible battery damage or control circuit damage and permitting a relatively compact battery to be used while, at the same time, limiting peak current in the motor windings, so as to allow the use of lower resistance windings and thereby increase efficiency in electric power usage across the entire power spectrum of the tool. By the same token, the motor can be made more compact while reducing the danger of motor overheating.

The present applicant has also provided for substantially instantaneous stoppage of motor rotation upon operator release of the trigger, to avoid the tendency of the motor to keep rotating for several turns, due to its own momentum, after trigger release. More particularly, applicant has recognized that one of the reasons that a surgeon may release the trigger of a rotary handpiece is that the bit, e.g. a rotary cutter, has accidentally become ensnarled in soft tissue. If the bit is allowed to continue rotation after the trigger is released, it will tend to start winding up such soft tissue with risk of injury to the surgical patient. The present applicant has found that dynamic braking, to avoid this problem, can be accomplished compactly and with few circuit components so as to minimize cost and assist in providing a compact, comfortably handed surgical handpiece.

Further objects and purposes of the invention will be apparent to persons acquainted with apparatus of this general type upon reading the following description and inspecting the accompanying drawings.

SUMMARY OF THE INVENTION

A compact surgical handpiece comprises a motor energizable for moving a tool member, an electric energy supply actuable for energizing the motor and a manually actuable trigger actuable to control motor operation. A motor control circuit interconnects the motor electric energy supply and trigger for running and braking the motor in response to actuation and release of the trigger. The control circuit includes a compact regulated voltage supply, a motor overcurrent limiting feature and a motor braking feature which is effective even if the operator fails to fully disconnect the electrical supply to the motor upon releasing the trigger.

DETAILED DESCRIPTION

The present invention relates to a control circuit 10 (FIGS. 1 and 2) for a surgical handpiece. The circuit 10 is usable with a variety of surgical handpieces for controlling the motors thereof but the handpiece 11 shown in FIG. 3 will suffice as an example. The FIG. 3 handpiece 11 includes a housing 12 of pistol shape having a barrel 13 and handle 14. A motor 15 drives a chuck 16 capable of receiving a material working member, or bit, 17. A trigger unit 20 is actuable by the surgeon or other user of the handpiece to control turning on and off of the motor 15 and to vary the speed thereof. A forward-disable-reverse (hereafter "reversing") switch 21 is actuable by the user to select between motor off and motor run forward and motor run reverse states. A battery 22 powers the circuit and thereby the motor 12 under the control of the trigger unit 20 and reversing switch 21. The control circuit 10 is usable with a variety of types of surgical handpieces, for example, ones for driving drills, reamers, sagittal saws, oscillating saws, reciprocating saws and the like.

The control circuit 10 is constructed so as to be as compact as possible so as to fit in and take up minimum room in the housing 12, thereby leaving more room for other components, including the battery 22 and motor 15 without compromising motor power and battery longevity.

Figure 1:
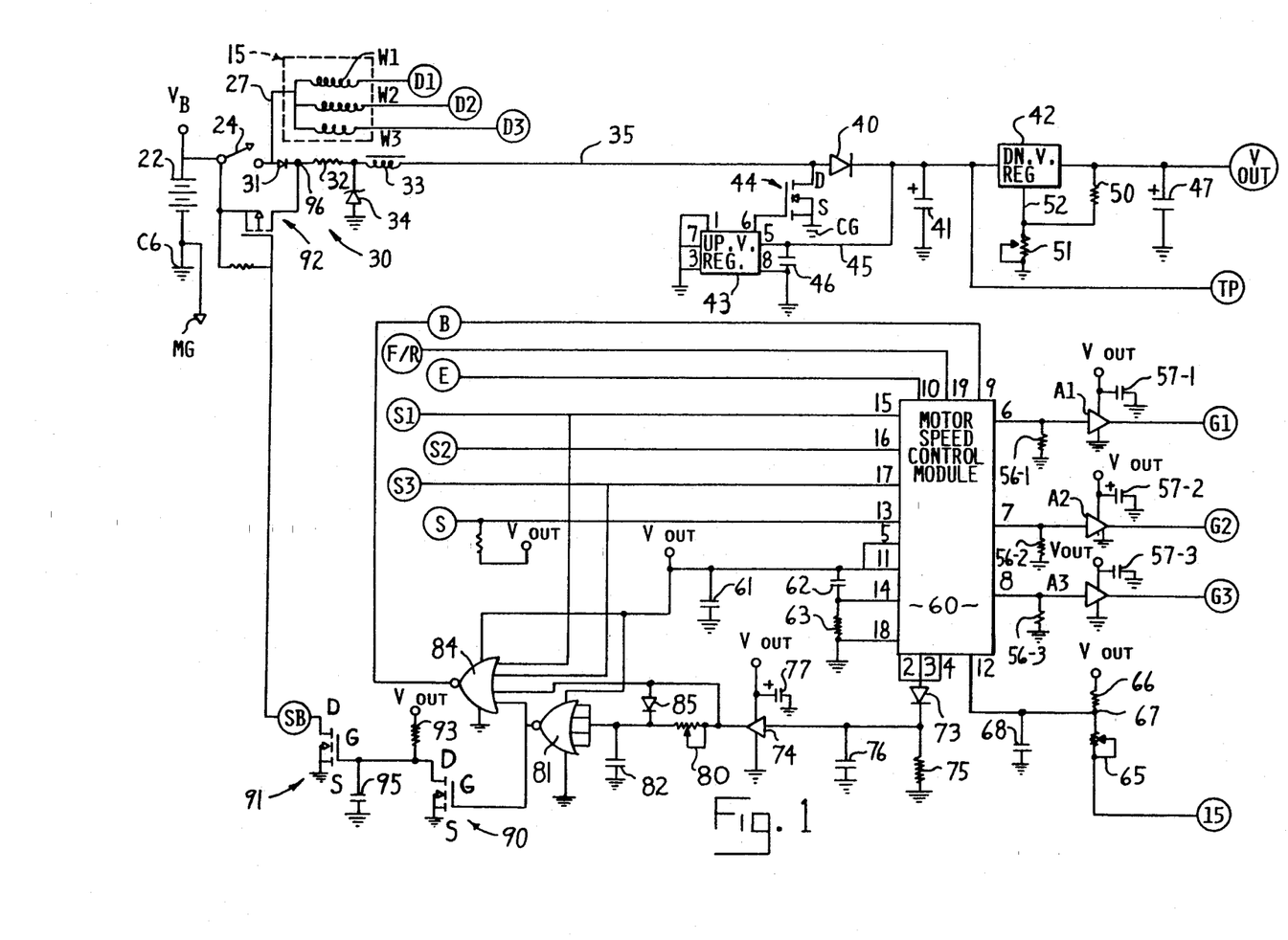
FIG. 1 is a schematic diagram of a portion of a control circuit for a surgical handpiece embodying the invention.

The motor 15 is, in the preferred embodiment shown, a brushless DC electric motor having a permanent magnet rotor (not shown) and stator windings, here three in number and indicated at W1, W2 and W3 in FIG. 1. Motors of this general type are well known. A suitable motor is available under Model No. 2296-100 from Stryker Corporation located at 420 E. Alcott Street, Kalamazoo, Mich. Such motors are compact and relatively efficient at converting electrical power to mechanical work.

The trigger unit 20 comprises a manually actuable trigger lever 23 (FIG. 4) coupled to an on/off switch 24 and a speed signal producer 25 capable of providing an output, here an analog voltage output, related to the desired motor speed, on a terminal S (FIG. 1). This speed signal producer 25 may be of any convenient type and one is shown schematically in FIG. 4, as incorporating a Hall sensor 26 connected as hereafter discussed and having a magnet MAG advanceable along the Hall sensor in response to further pressing of the trigger 20 to change the analog voltage on the speed signal terminal S. Thus, initial movement of the trigger 20 from its rest position closes the switch 24 and starts the rightward advance (FIG. 4) of the magnet MAG to decrease the voltage at speed signal terminal S to thereby call for more motor speed.

The battery 22, as shown in FIG. 1, has its positive voltage output terminal marked VB and its negative terminal is connected to two separate ground buses, as follows. A high current draw ground bus MG serves as the motor current ground and carries the triangular ground symbol. A low current draw ground bus CG serves as the control logic ground and carries the usual triple line ground symbol.

The on/off switch 24, when closed, connects the positive battery terminal VB through a line 27 (FIG. 1) connected in common to the input end (left end in FIG. 1) of all three of the motor windings W1, W2 and W3 for energizing same as hereafter discussed. The on/off switch 24, when closed, also supplies positive voltage from the positive battery terminal VB to a regulated voltage supply circuit indicated generally at 30 in FIG. 1.

The supply 30 comprises a line, connectible to the positive battery supply VB by the switch 24 and including, in series, a diode 31, a resistor 32 and an inductor 33 leading to a line 35. A Zener diode 34 has its cathode connected between the resistor 32 and inductor 33 and its anode connected to control circuit ground CG. The diode 31 is oriented for current flow from the switch 24 to the line 35. The Zener diode 34 limits the DC voltage applied to the line 35 with the switch 24 closed.

A diode 40 has its anode connected to the voltage input line 35 and its cathode connects to several elements, namely a capacitor 41 in turn connected to control circuit ground, a voltage test print TP and the input of a step down voltage regulator 42. A step up voltage regulator 43 has a pin 6 connected to the control electrode (gate) of a field effect transistor (hereafter FET) 44. The FET 44 has its drain and source electrodes connected from the anode of the diode 40 to control circuit ground CG. The step up voltage regulator 43 has a pin 5 connected by a feedback line 45 to the cathode side of the diode 40. Remaining pins 1, 7, 3 and 8 connect to ground CG as shown and a capacitor 46 connects across pins 5 and 8 of the regulator 43. The ground connections of pins 1, 7, 3 and 8 is conventional. The capacitor 46 is a conventional loop gain compensation capacitor to change the response time of the regulator 43 to compensate for different loads.

The step down voltage regulator 42 has an output going to a voltage output pin VOUT. A capacitor 47 connects that output to control circuit ground CG. A voltage divider comprising a resistor 50 and calibratable resistor 51 in series connects from the voltage output line VOUT to control circuit ground CG. A point intermediate the resistors 50 and 51 connects to a voltage level control input 52 of the step down voltage regulator 42, the calibratable resistor 51 being manually presettable to determine the voltage on output pin VOUT.

The step up voltage regulator 43 is a model Max 643A, manufactured by Maxim Integrated Products, located at 120 San Gabriel Drive, Sunnyvale, Calif. The step down voltage regulator 42 is a model LM117K, manufactured by National Semiconductor Corporation located at 2900 Semiconductor Drive, Santa Clara, Calif.

The step up voltage regulator 43 turns on and off the FET 44 at a relatively high frequency, here for example 50 kilohertz. The turned on FET 44 pulls current through the coil 33 which stores energy in the coil 33. When the FET 44 turns off, the energy stored in the coil 33 is released through the diode 40. Thus, the regulator 43, FET 44 and coil 33 act substantially as a flyback circuit wherein a voltage is produced on the cathode of the diode 40 (for example 15 volts) which is higher than the battery voltage VB (for example 12 volts). The capacitor 41 eliminates some, though not all of the rather substantial amount of ripple on the voltage appearing on the cathode of diode 40.

The line 45 feeds back the voltage at the cathode of diode 40 to the step up voltage regulator 43 so as to keep the average voltage level at the cathode of diode 43 substantially constant (ignoring the superposed ripple) despite changes in the instantaneous level of the postivie battery terminal VB in turn resulting from changes in the load on the bit 17 and hence on the motor 15. In extreme circumstances, the voltage of battery VB can vary between 4 volts and 15 volts depending on the load imposed thereon and the battery's state of charge. The step up voltage regulator 43 and FET 44 cooperate with the inductor 33 and diode 40 to maintain the cathode of diode 40 at about 15 volts DC with ripple superimposed on it.

The high frequency of the on/off cycle of the FET 44 established by the step up voltage regulator that it keeps the inductor 33 from saturating and allows it to be of small physical size. The capacitor 41 can also be of small physical size in view of the high frequency of the ripple and the fact that the capacitor 41 is not required to eliminate all the ripple.

The step down voltage regulator 42 eliminates the vast majority of the ripple in the voltage appearing in the output of diode 40 and steps the voltage down to 12 volts applied to the regulated output voltage terminal VOUT. In the circuit shown, the step down voltage regulator 42 changes the approximately 15 volts input, including about a volt and a half of the ripple, to 12 volt level with negligible ripple (for example a maximum of 200 millivolts of ripple) superimposed thereon.

The capacitor 47 helps to minimize the ripple at the output of the step down voltage regulator 42 and also helps to maintain the 12 volt desired level at the regulated voltage output pin VOUT by partially discharging thereto in the presence of a brief but substantial transient increase in the load served by the regulated voltage positive output pin VOUT.

Applicant has found that an attempt to provide a consistent fixed control circuit voltage supply at terminal VOUT, without the step up and step down regulators 43 and 42, using one or more capacitors at 41 at the output of a conventional regulator, would be very difficult in view of the wide swings of the voltage VB with load and would require a physically very large capacitor, one whose size would be intolerably large in a circuit that needs to be compact so as to fit in to the small space in a compact handheld surgical instrument. Further, the small inductor 33 and capacitors 41 and 47 are much more immune to the heat and moisture encountered in steam sterilizing the surgical handpiece 11 in an autoclave. The inductor 33, basically a wire wrapped around a ferrite core, is much more immune to autoclave damage than would be a large capacitor such as the typical large electrolytic capacitors often used in ripple reduction in power supplies.

The control circuit 10 includes a conventional motor speed control module 60 (FIG. 1). In the embodiment shown, the module 60 is a Model LS7262 available from LSI Computer Systems of Melville, N.Y.

Pins 5 and 11 of the module 60 receive positive operating potential from the regulated voltage output pin VOUT. A capacitor 61 passes to circuit ground CG any transient voltage spikes that may occur upon turn-on on turn-off of the positive regulated voltage at VOUT and is connected to module pins 5 and 11.

A further capacitor 62 and resistor 63 connect in series from the regulated positive voltage supply pin VOUT to circuit ground CG. Module pin 14 connects between the capacitor 62 and resistor 63 and module pin 18 connects to circuit ground CG.

The series capacitor 62 and resistor 63 act as an RC timing circuit connected to pin 14 of the motor speed control module 60. The conventional module 60 includes an oscillator(not shown), the frequency of which is set at the pin 14 by the RC timing circuit 62, 63. In the embodiment shown, the oscillator frequency was selected to be about 400 Hz. The conventional module 60 also includes a sequencer (not shown) which initiates positive output pulses on the module output pins 6, 7 and 8 in sequence (initiates a pulse to pin 6, then initiates a pulse to pin 7, then initiates a pulse to pin 8, then initiates a pulse to pin 6 to start the sequence over again). The rotor position is decoded by Hall sensors connected to S1, S2 and S3. The decoded signal determines which output pin is turned on. The amount of "on" time while the rotor is in the proper position is controlled by pulse width modulation (PWM). The PWM frequency is set by the RC timing circuit 62, 63. The PWM works together with the S signal from the trigger, to determine the proper amount of "on" time. The above determines the energy applied by current pulses through the winding W1 and FET F1 (as well as the windings W2 and W3 and corresponding FETs F2 and F3).

Figure 2:
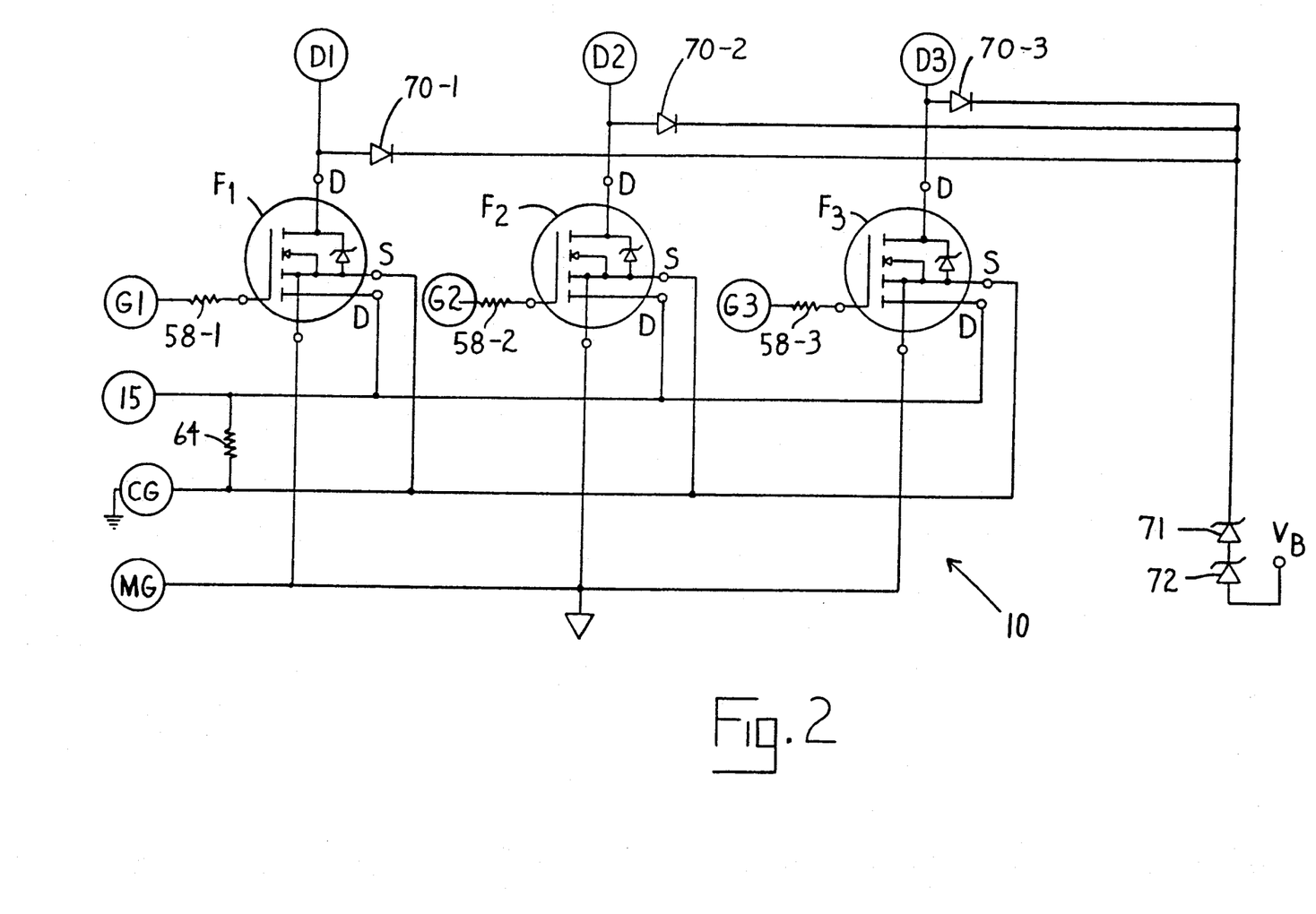
FIG. 2 is a schematic diagram of an additional portion of the control circuit of FIG. 1, specifically providing for control of current flow to the motor windings.

The motor speed control module 60 has motor drive pins 6, 7 and 8 (FIG. 1) which, during normal operation of the motor 15, produce variable time length, positive output, voltage pulses which are amplified by corresponding amplifiers A1, A2 and A3 and applied to corresponding control electrodes G1, G2 and G3 of corresponding FETs F1, F2 and F3 (FIG. 2).

Resistors 56-1, 56-2 and 56-3 connect from the control module output pins 6, 7 and 8 respectively to control circuit ground CG to pull down the open emitter outputs of control module 60. The amplifiers A1–A3 each are connected across the regulated voltage output VOUT and control circuit ground and have a respective capacitor 57-1, 57-2 and 57-3 from their positive DC voltage input pin to control circuit ground CG to stabilize such amplifier positive supply voltage input pin in a conventional way.

The gate pins G1, G2 and G3 each connect to the corresponding gate (FIG. 2) of their respective field effect transistors F1, F2 and F3 through respective anti-oscillation resistors 58-1, 58-2 and 58-3.

The drain electrodes of the FETs F1, F2 and F3 connect, as respectively indicated at D1, D2 and D3 (FIGS. 1 and 2) to the free ends of the respective motor windings W1, W2 and W3. The FETs F1, F2 and F3 are double FETs, each having a common control electrode (gate) and a common sources but two drains D and D'. Such double FETs are also referred as sense FETs (or SENSFETs)in that the extra drain D' of each can be used to sense the instantaneous level of current flow through the corresponding FET and thus through the corresponding motor winding W1, W2 or W3.

The common source S of each FET F1, F2 and F3 further connects to the low current (control circuit) ground bus CG. The extra drains D' of the FETS F1–F3 connect in common to a motor load indicator line IS. A resistor 64 connects from the motor load line IS to the resistance which is large (in this instance 1,000 ohms) compared to the very low series resistance of any motor winding W1, W2 or W3 and its series FET F1, F2 or F3 when that FET is fully conductive. Accordingly, when a given FET F1, F2 or F3 is conductive, almost the entire voltage drop across the FET appears across the resistor 64. Accordingly, the voltage appearing on the terminal IS is substantially proportional to and hence a valid measure of the instantaneous current drawn by the motor and hence to the load on the motor.

In addition, note that the resistance of a conductive FET changes with temperature. Thus, the voltage drop across the resistor 64 will also be influenced by the operating temperature of the FETS F1, F2 and F3. Thus, the voltage level on the indicator pin IS will also indicate if one or more of the FETS F1–F3 is overheating and in danger of destroying itself.

The resistor 64, through the pin IS, connects in series with a calibratable resistor 65 (FIG. 1) and fixed resistor 66 in turn connected to the regulated positive voltage supply terminal VOUT. Accordingly, the resistances 66, 65 and 64 form a voltage divider connected from the regulated positive voltage supply pin VOUT to control circuit ground. A point 67 between the resistors 66 and 65 connects to a safety input pin 12 of the motor speed control module 60. When the voltage level at the junction point 67 (and pin 12 of the control module 60) reaches a threshold level (here about 6 volts) preset by adjustment of the variable resistor 65, and indicating that the motor is overloaded (the motor windings W1, W2 and/or W3 have excessive current flow therethrough) or/and indicating overheating of one or more of the FETS F1–F3, the module 60 shuts off the FETS F1–F3 and thereby shuts off the motor 15. A capacitor 68 connected to the pin 12 shunts any transient voltage spikes to ground and thereby prevents rapid turning on and off (hunting) of the FETS F1–F3 and motor 15 by reason of rapid oscillating of the voltage at pin 12 back and forth across its threshold.

Hall sensors S1, S2 and S3 (FIGS. 1 and 3) conventionally signal the instantaneous rotational position of the rotor (not shown) of the motor 15. The sequencer (not shown) in the conventional motor speed control module 60 initiates pulses on motor speed control module output lines 6, 7 and 8 (FIG. 1) in response to respective signals from the Hall sensors S1, S2 and S3. The purpose is to energize the proper one of the windings W1, W2 and W3 (FIG. 2) at the proper time depending on the position of the rotor of the motor 15 indicated by the motor Hall sensors S1, S2 and S3 so as to forwardly or rearwardly run the motor.

The analog voltage speed signal applied to terminal S, and hence to motor speed control module pin 13 from the trigger position sensor 26 in the trigger unit 20, controls the length of each pulse supplied to the gate of each of the motor drive FETs F1, F2 and F3 and thereby determines the amount of energy applied to the motor windings and hence the motor speed. In the FIG. 4 embodiment, the trigger position sensing Hall sensor receives operating potential by connection to the regulated positive output pin VOUT and circuit ground CG and applies its speed signal to pin S. Two wires connect Hall sensor 26 to terminal VOUT to avoid calling for maximum motor speed if one wire should accidentally be broken.

Figures 3, 5:
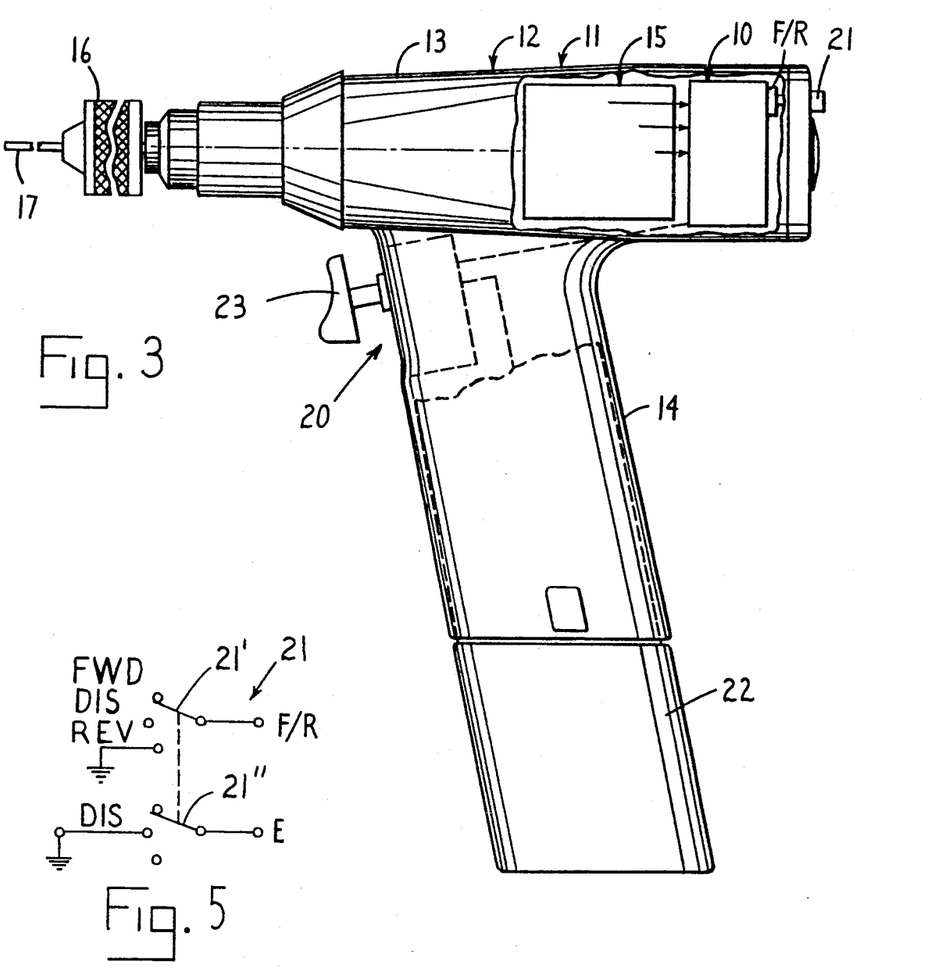
FIG. 3 is a schematized, partially broken elevational view of a surgical handpiece embodying the invention.
FIG. 5 is a schematic diagram of a suitable forward-disable-reverse switch usable with the FIG. 3 handpiece.

The forward-disable-reverse switch 21 may be of any convenient type. A schematic example is shown in FIG. 5. The output voltage supplied through the corresponding reversing pin F/R to the motor speed control module reversing pin 19 causes the sequencer in the module 60 to shift the timing of the corresponding outputs to the gates G1–G3 of the FETs F1–F3 with respect to the outputs from the Hall sensors S1–S3 to cause the motor 15 to run in reverse, when the switch 21 is shifted from its forward to reverse position. With the switch 21 in its disable position, the motor speed control module 60 decouples the trigger signal on pin S (pin 13 of module 60) from the motor drive pins 6, 7 and 8 thereof so that the motor will not run.

The rightward (FIG. 1) ends of the motor windings W1, W2 and W3, which connect to the respective drains of the FETs F1, F2 and F3 respectively, also have respective current paths through respective diodes 70-1, 70-2 and 70-3 to a common series pair of Zener diodes 71 and 72 and thence to the positive battery terminal VB. This protects the drains D1, D2 and D3 of the FETs F1, F2 and F3 from appearance of an excessively high voltage thereon at the end of each current pulse drawn by a given FET F1, F2 or F3 through its corresponding winding W1, W2 or W3, wherein the corresponding winding W1, W2 or W3, still stores energy due to such current flow therethrough, faces the suddenly greatly increased resistance of the corresponding FET F1, F2 or F3 occurring when that FET turns off. Absent a path to discharge that energy, the rapid turn-off of the FET and the energy still stored in the corresponding winding would produce a high voltage pulse on the drain D1, D2 or D3 of the corresponding FET since the effective resistance of the FET has gone from near zero to near infinity. To avoid damage to the FET and other possible disruptive effects of such a high voltage spike appearing at the connection of the FET drain to the corresponding winding, the corresponding diode 70-1 or 70-2 or 70-3 allows the part of the voltage spike substantially above positive battery voltage VB (by an amount, here 15 volts, established by the Zener diodes 71 and 72) to pass to the positive battery terminal VB, as if it were attempting to recharge the battery VB. This limits the overvoltage of the spike appearing on the corresponding FET drain to a tolerable level. The diodes 70-1, 70-2 and 70-3 isolate the FET drains D1, D2 and D3 from each other so that energy discharging from, for example, the coil W1 upon shutoff of the FET F1 and passing to the common connection to the first Zener diode 71, is blocked by the diodes 70-2 and 70-3 from reaching the FETs F2 and F3.

In releasing the trigger on the handpiece it would be possible in some handpieces that the operator might stop the release before there was a complete opening of the switch 24 but wherein the speed signal on terminal S signal zero speed, in other words leaving the motor control module 60 in an ambiguous condition. The braking circuit hereafter described is intended to overcome this possibility, as well as to provide for rapid halting of the tool bit when the trigger is released sufficient to make the terminal S call for zero speed, even if the switch 24 still be closed.

To promptly stop rotation of the motor and movement of the bit 17 promptly upon release of the trigger 23 by the operator, the control circuit 10 is provided with a dynamic braking circuit, as follows. The conventional motor speed control module 60 is provided with a second triplet of motor drive pins 2, 3 and 4 which are energized in synchronism with the above-discussed motor drive pins 6, 7 and 8. This is because the particular module 60 here provided was designed to allow so-called full wave three-phase motor operation. However, in the present invention, the motor speed control module 60 is used only as a half wave motor speed control, in that only above-discussed pins 6, 7 and 8 are used for driving the motor 15. The motor drive pins 2, 3 and 4 are thus in effect "left over". The present invention uses such "left over" motor drive pins 2, 3 and 4 for braking, rather than running, the motor 15. Thus, when the motor is to be shut off and the positive motor drive signals disappear from the drive pins 6, 7 and 8, and from pins 2, 3 and 4. Thus, the voltage on pins 6, 7 and 8 and on pins 2, 3 and 4 goes to a steady low. The appearance of such a steady low signal from pins 2, 3 and 4 as soon as the positive (high) drive signals disappear from drive pins 6, 7 and 8 is highly useful because it allows Applicant's circuit to immediately brake the rotation of the motor and avoids the possibility of the motor simply coasting due to the inertia of its rotor, when the trigger is released.

More particularly, the module pins 2, 3 and 4 are here connected together and any positive signal appearing thereon passes through a diode 73 to the input of a buffer amplifier 74. A resistor 75 connected from the cathode of diode 73 to control circuit ground CG allows the voltage on the input of buffer amplifier 74 to rise above ground in response to conduction through the diode 73. A capacitor 76 connects to the input to the buffer amplifier 74 and provides filtering when PWM output is less than 100%. The buffer amplifier 74 is conventionally connected to receive positive operating voltage from the regulated positive voltage supply VOUT and to control circuit ground CG, as with amplifiers A1, A2 and A3 above described. Similarly, a capacitor 77 to ground CG stabilizes the positive voltage supply to the amplifier 74.

The output of amplifier 74 connects through a calibratable resistor 80 to the ganged inputs of a NOR gate 81. A capacitor 82 connects between the ganged inputs of the NOR gate 81 and control circuit ground CG. The output of the buffer amplifier 74 also connects to one input of a second NOR gate 84. The second NOR gate 84 has further inputs connected to two of the motor rotor position sensing, Hall sensor outputs (here S1 and S3). The second NOR gate 84 has a final input connected to the output of the first mentioned NOR gate 81. The NOR gates obtain their required operating potential from connection to the regulated voltage positive output line VOUT and to control circuit ground. The output of the NOR gate 84 connects through the brake signal line B to the brake activating terminal 9 of the motor speed control module 60. The circuitry controlling the brake signal line B is completed by a diode 85 connected to pass current from the output of amplifier 74 to the upper end of the capacitor 82.

It is convenient to use the terms "high" and "low" to refer to voltage levels nearer the positive 12 volts VOUT level and the ground level CG, respectively, in the following discussion.

The above described brake signal circuit works as follows. With the motor speed control 60 applying positive pulses to the output lines 6, 7 and 8 thereof, to run the motor 15, corresponding positive pulses appear on the ganged output pins 2, 3 and 4 of the module 60. Thus, while the motor is running, such positive pulses charge the capacitor 76 and cause the buffer amplifier 74 to charge the capacitor 82 through the diode 85 and allows substantially instantaneous charging of the capacitor 82. This shifts the input of NOR gate 81 high so that its output is low. This makes the corresponding input of the second NOR gate 84 low. However, the other inputs of second NOR gate 84 are high in view of the high applied from the output of the buffer amplifier 74 and also in view of the periodic high potential pulses outputted from Hall sensors S1 and S3 to corresponding inputs of the second NOR gate 84. In consequence, the output of the second NOR gate 84 is low, meaning that the motor speed control module 60 is not being told to brake.

Note that the module 60 must run the motor before it can dynamically brake the motor. This avoids applying braking current to the motor windings prior to running of the motor and hence prior to use of the tool. When the operator releases the trigger 23, the speed signal terminal S goes high as does corresponding pin 13 on module 60. This causes the module drive pins 6, 7 and 8 and similar pins 2, 3 and 4 to go low. The capacitor 76 can now discharge through the resistor 75, allowing the buffer amplifier 74 to turn off and provide a low on its output. This drops the right side of calibrated resistor 80 to circuit ground potential and the capacitor 82 discharges through the variable resistor 80 in a delay time established by the setting of the variable resistor 80. This delay time is selected to allow time for braking and not allow the continuance of braking current through the windings of the motor 15 after the motor 15 has had plenty of time in which to come to a stop. In other words, it is desirable, to minimize drain on the battery 22 and heating of the motor windings W1, W2 and W3, to cease flow of braking current through the motor windings after the motor has stopped. Timing out of the RC time delay unit 80, 82 serves this purpose. In the embodiment shown, the RC delay unit 80, 82 is set to time an interval of about ½ second.

Returning to the time at which the RC delay timing unit 80, 82 starts the time out and the low voltage is applied from buffer amplifier 74 to the corresponding input of the second NOR gate 84, the NOR gate 84 experiences a low on its two lower input pins and experiences periodic lows on its two upper pins, namely between the Hall sensor pulses on Hall sensor outputs S1 and S3. The result is initiation of a series of positive voltage (high) pulses on the output of second NOR gate 84 and hence through the brake line B to the brake signal input pin 9 on the motor speed control module 60. The conventional module 60 reacts to these positive braking pulses by causing the FETs F1-F3 to apply pulses of dynamic braking current to the motor windings W1, W2 and W3 in a manner to dynamically brake, i.e. rapidly decelerate, the motor 15.

If the Hall sensor outputs S1 and S3 were not inputted to the second NOR gate 84, the low potential from buffer amplifier 74 to the corresponding input of the second NOR gate 84 would cause it to produce a continuous high on the motor speed control module 9, causing it to apply braking current to the motor 15 so severely as to virtually instantaneously stop motor rotation. The result undesirably could be a torque reaction strong enough to tend to jerk the handpiece out of the hand of the user, because of the inertia of the motor rotor and associated output mechanism (for example gear train, output shaft, chuck, etc.). Thus, connecting outputs from Hall sensors S1 and S3 to inputs of the second NOR gate 84 causes the positive output signal applied thereby to the brake signal line B to be pulsed rather than continuous, and such that the timing of the pulses is a function of the instantaneous speed of the motor. As a result, braking torque on the motor starts at less than maximum and increases until the motor stops.

Shortly after the motor stops, as above discussed, the RC timing unit 80, 82 times out causing the input and output of the first NOR gate to respectively go low and high. The latter high is applied to the corresponding input of the second NOR gate 84 and therefore switches its output low, turning off the brake signal. As above mentioned, the module 60 cannot thereafter apply braking current to the motor windings until after it has run the motor again.

Figure 4:
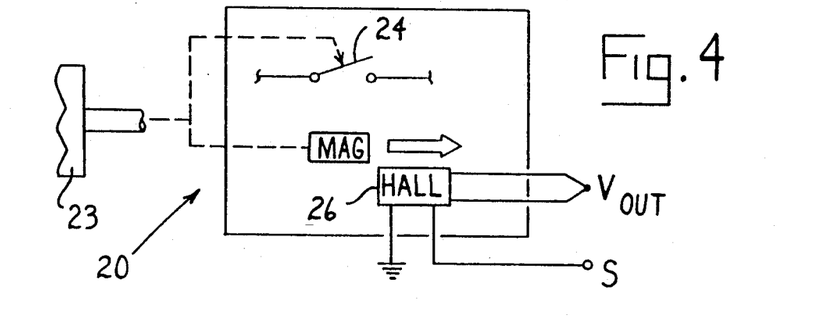
FIG. 4 is a schematic diagram of the trigger unit of the FIG. 3 handpiece.

In summary, it will be seen that even if the on/off switch 24 does not open as the operator releases the trigger 23 (for example due to failure of the operator to fully release the trigger 23 or due to the switch 24 somehow hanging closed) leftward movement of the permanent magnet MAG, in FIG. 4 back to its leftmost "off" position will cause the module 60 not only to stop actuating the motor 15 for rotation, but also, in combination with the NOR gates 81 and 84, will actually cause dynamic braking of the motor 15 to bring it swiftly to a stop.

On the other hand, assume that upon release of the trigger 23 by the operator, the switch 24 properly opens. In that case, the battery positive terminal VB is no longer connected by the switch 24 to terminal VIN. Thus, the regulated voltage supply 30 would be shut off and no regulated positive voltage would appear on the terminal VOUT. If no voltage VOUT is available, the module 60 and its associated circuit have no operating potential and thus cannot apply dynamic braking to the motor 15 in the manner above described. To avoid this problem, additional FETs 90, 91 and 92 (FIG. 1) are provided as follows.

The FET 90 has its drain connected through a pull-up resistor 93 to the positive regulated voltage pin VOUT and has its source S connected to control circuit ground. The gate of FET 90 is connected to the output of first NOR gate 81. The next FET 91 has its drain connected through a line SB and a pull-up resistor 94 to the positive battery terminal VB and has its source connected to control circuit ground. The gate of the second FET 91 connects to the drain of the first FET 90. A capacitor 95 provides a time delay to prevent bypass oscillation during power down. The third FET 92 has its drain and source connected respectively to the battery positive terminal VB and to a point 96 intermediate the cathode of diode 31 and the resistor 32 of the regulated voltage supply 30.

When the operator first pulls the trigger 23, and the switch 24 closes, the regulated voltage supply 30 applies a regulated positive voltage to the pin VOUT as above described. A further pull on the trigger moves the magnet MAG with respect to the hall sensor HALL in the FIG. 4 trigger unit 20 to thereby decrease the voltage on the speed line S to pin 13 of the motor speed control module, which causes the module to turn on the motor 15 and run it at the speed required by the partially or fully pulled trigger 23. The resulting positive output applied from module pins 2, 3 and 4, buffer amplifier 74 and diode 85 to the inputs of the first NOR gate 81 pulls the output of such NOR gate 81 low. This renders the first FET 90 open. The resultant high on the gate of the second FET 91, provided through resistor 93 after capacitor 95 charges, turns it on and the resultant voltage drop across the resistor 94 and now conductive second FET 91 pulls the gate of the FET 92 low and turns it on. The now conductive FET 92 provides a low resistance shunt from the positive voltage battery terminal VB across the on/off switch 24 and diode 31 to supply sufficient operating current to the regulated voltage supply 30 as to provide the required positive regulated voltage on its output VOUT even if the switch 24 is open, due to a full release of the trigger 23 by the operator, for example.

As discussed above, a release of the trigger 23 by the operator first returns the magnet MAG (FIG. 4) to its original position calling for zero motor speed and the motor speed control module responds to the resulting maximum positive potential applied by line S to its pin 13 by dropping low the potential on its motor drive pin 6, 7 and 8 and spare motor drive pins 2, 3 and 4. As discussed, the RC time delay unit 80, 82 begins gradually to time out, while the NOR gates 81 and 84 apply the brake signal to pin 9 of the motor speed control module so that the latter effects dynamic braking in the manner above discussed. Note that during this dynamic braking period (while the RC timing circuit 80, 82 times out) the output of the first NOR gate 81 stays low so that the FETs 91 and 92 stay on. Thus, even if trigger release has allowed the switch 24 to open, the conductive FET 92 allows the regulated voltage supply 30 to maintain a regulated high positive potential on its output pin VOUT to power the remainder of the FIG. 1 circuit.

Note that the diode 31 prevents the motor windings W1, W2 and W3 from drawing current through line 27 when the switch 24 is open even though the FET 92 may be turned on. This avoids the risk that the motor windings W1, W2 and W3 may attempt to draw more current through the FET 92 (with the switch 24 open) than the FET 92 can supply thereby risking damage to the FET 92 and in effect stealing current which the FET 92 needs to supply to the module 60 and associated control logic.

When motor braking is finished and the RC delay unit 80, 82 at some time shortly thereafter times out, the output of NOR gate 81 swings high. This not only stops the brake signal by action on the second NOR gate 84, but also turns on the FET 90, which in turn turns off the FET 91 and thereby the FET 92. The FET 92 in its off condition acts like extremely high resistance, for all practical purposes an open circuit, and thereby decouples the regulated voltage supply circuit 30 from the positive battery terminal VB. As a result, the control circuit 10 shuts down.

The reversing switch 21 (schematically shown, by way of example, in FIG. 5) has a pair of movable contacts 21' and 21" and two corresponding sets of fixed contacts. The first movable contact 21' is shiftable between forward and reverse positions to respectively connect an open and the control circuit ground CG, to the forward/reverse line F/R leading to corresponding pin 19 of the motor speed control module 60 to change from forward to reverse motor rotation. In the middle position (the disable position) of the switch 21, the second movable contact 21" connects the control circuit ground CG to the disable line E and thereby to disable pin 10 of the motor speed control module 60 which positively prevents the module 60 from energizing the motor 15, as an additional safety factor. Thus, unless the reversing switch 21 is physically shifted by the operator from its disable position to either its forward or reverse position, the motor 15 cannot be run.

OPERATION

The foregoing discussion sets forth in detail the operation of the apparatus embodied in the invention. However, the following comments will briefly summarize same for convenient reference.

The regulated voltage supply 30 provides a constant 12 volt regulated output over the approximate 4 volt to 14 volt input range of the battery 22, depending on the load imposed on such battery. Such is permitted by the arrangement of the dual regulators 43 and 42 in series. The step up regulator 43 converts the varying battery voltage to a constant 15 volt output. The step down regulator converts the 15 volts to a 12 volt output. This arrangement provides a cleanly regulated 12 volt dc output without need for physically large filter capacitors and thus reduces the amount of surface area of the circuit required for packaging. The reduced size and capacitance in the output of the step up regulator 43 leaves a substantial amount of ripple in the 15 volt output, but the 12 volt step down regulator eliminates that ripple effectively.

The motor speed control module 60 handles all motor control functions. The motor windings W1, W2 and W3 are switched by the corresponding SENSFETs F1, F2 and F3. The SENSFETs F1, F2 and F3 also return a voltage signal to the module 60 to provide current limiting. The feedback signal is proportional to the "on" resistance of the SENSFETs and not to the resistance ratio of the two sections of the SENSFETs. Since FETs resistance increases with temperature, by using the "on" resistance of the FETs to provide a current limit signal, increased temperature will decrease the current limit, further safeguarding the FETs and motor windings.

Turning to the brake circuit including gates 81 and 84, the motor speed control module 60 here provides drive signals for full wave motor operation. Since the present circuit is being used in the half wave mode, the three motor drive signals appearing at module terminals 2, 3 and 4 are not used to run the motor 15. Combining and filtering these three signals at pins 2, 3 and 4 produces a signal appropriate to cause motor braking. The signal, as applied to the buffer amplifier 74, is available the instant that the motor run signal at motor speed control module pins 2, 3 and 4 and 6, 7 and 8 is removed and requires no calibration as would a separate switch or a comparator brake signal. The brake signal on module pins 2, 3 and 4 is high when the motor is running and low when the motor stops running. With the motor running, the signal from module pins 2, 3 and 4 instantaneously charges the capacitor 82 through the diode 85. The same capacitor 82 discharges through the larger resistor 80 to provide a time delay. The time delayed brake signal i then inverted by the NOR gate 81 and gated by the NOR gate 84 with the original brake signal. This guarantees that the motor must run before braking can happen and that braking can happen only for the amount of time allowed by the RC time constant of capacitor 82 and resistor 80. Also gated with the brake signal and delayed brake signal at the input of NOR gate 84 are signals from all sensor lines S1 and S3 proportional to the motor commutation signal. This provides control over the torque reaction or kick that would be produced by instantaneous stopping of the motor rotor. The motor commutation signals from Hall sensors S1 and S3 is a square wave signal at a fifty percent duty cycle and its frequency decreases as motor speed decreases; therefore its period, or "on" time increases as speed decreases. This means that the slower the motor is turning, the higher the braking torque applied to the motor rotor.

Also provided by the above discussed brake circuitry is a bypass 92 for the on/off switch 24. This is necessary since when the trigger is released, the on/off switch 24 is normally opened, which would remove power from the regulated power supply 30 and hence the remaining logic in the control circuit 10, and yet this is the same time during which braking would need to take place. Because the motor speed control module 60 still needs power to complete braking, the on/off switch 24 is bypassed by turning on the FET 92, but not the motor windings W1, W2 and W3, for the amount of time that the dynamic braking of the motor rotor is to occur.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical handpiece comprising:
   a motor energizable for moving a tool member;
   a compact electrical energy supply means having an output voltage substantially variable in amplitude inversely with load, so as to drop substantially below it nominal voltage output in response to a substantial load thereon;
   control means actuable for energizing said motor from said electrical energy supply means;
   a regulated DC voltage supply energized by said electrical energy supply means for supplying constant amplitude operating voltage to said control means despite load induced variations in the voltage output of said electrical energy supply means, said regulated DC voltage supply being of minimal physical size to take minimum room in said handpiece, said regulated DC voltage supply comprising:
   step up voltage regulator means connected to said electrical energy supply means and responsive thereto for producing a ripple topped voltage output exceeding the nominal voltage of said electrical energy supply means;
   step down voltage regulator means connected to the output of said step up voltage regulator means and driven by said output thereof for removing substantially the entire ripple and reducing said voltage output substantially to the nominal voltage output of said electrical energy supply means.

2. The apparatus of claim 1 in which said step up voltage regulator means comprises an inductor, junction point, diode and capacitor connected in series from one side of said electrical energy supply means to the other side thereof, a step up voltage regulator having an oscillatory output voltage, an electronic switch having a control electrode driven by said oscillatory output voltage of said step up voltage regulator, said electronic switch having a main current path therethrough connected between said junction point and the other side of said electrical energy supply means for turning on and off current flow in a loop including said electrical energy supply means, inductor, junction point and electronic switch and for doing so at a frequency corresponding to the frequency of said oscillatory output voltage of said step up voltage regulator and thereby producing a voltage with a corresponding frequency component inputted to said diode and of amplitude exceeding the nominal voltage of said electrical energy supply means, said capacitor being of minimal physical size so as to remove only a part of the corresponding frequency ripple from the output of said diode;
   said step down voltage regulator means comprising a step down voltage regulator responsive to the output of said diode for removing substantially the entire ripple from the diode output voltage while reducing the voltage thereof substantially to the nominal voltage of said electrical energy supply means and doing so despite the load responsive variations in the voltage output of said electrical energy supply means.

3. The apparatus of claim 1 in which said step up voltage regulator means comprises a step up voltage regulator having an oscillatory output voltage, an electronic switch having a control electrode driven by said oscillatory output voltage of said step up voltage regulator, said electronic switch having a main current path therethrough connected in a circuit loop with said electrical energy supply means for turning on and off current flow in said loop at a frequency corresponding to the frequency of said oscillatory output voltage of said step up voltage regulator and thereby producing a voltage with a corresponding frequency component and of amplitude exceeding the nominal voltage of said electrical energy supply means.

4. The apparatus of claim 3 in which said step up voltage regulator means comprises a diode connected for applying said produced voltage to said step down voltage regulator means, said step down voltage regulator means comprising a step down voltage regulator responsive to the output of said diode for removing substantially the entire ripple from the diode output voltage while reducing the voltage thereof substantially to the nominal voltage of said electrical energy supply means and doing so despite the load responsive variations in the voltage output of said electrical energy supply means.

5. The apparatus of claim 1 including manually actuable trigger means actuable for requesting motor operation, said control means being actuable by said manually actuable trigger means for energizing said motor from said electrical energy supply means, said control means including a plurality of motor drive terminals actuable for providing motor drive signals suitable for full wave motor operation, said plurality comprising first half wave motor drive terminals and second half wave motor drive terminals, said first terminals being interconnected for running said motor in a half wave mode in response to actuation of said manually actuable trigger means.

6. The apparatus of claim 5 including brake actuating means connected to said second half wave motor drive terminals and responsive to cessation of said motor drive signals for producing a braking signal, and means responsive to said braking signal for braking said motor.

7. The apparatus of claim 6 in which said brake actuating means comprising delay timing means operatively connected to said second half wave motor drive terminals and enabled in response to running of said motor by said control means and responsive to said cessation of said motor drive signals on said second half wave motor drive terminals for timing an interval sufficient to allow said motor to be braked to a stop, said timing means disabling said braking means and thereby preventing further braking of said motor, upon completion of said timing, said delay timing means permitting braking of said motor by said braking means during timing of said interval.

8. The apparatus of claim 6 in which said brake actuating means includes gate means responsive to the absence of drive signals from said motor drive terminals for providing said braking signal, means responsive to rotor position in said motor for applying commutation signals to said control means for proper timing of motor drive signals to said motor by said control means, means connecting at least one of said commutation signal applying means to said gate means for modulating said braking signal to increase the braking torque on the motor as the motor slows, so as to prevent the motor from trying to jerk the handpiece out of the hand of the user upon initiation of braking of the motor.

9. The apparatus of claim 6 in which said trigger means includes a manual on/off switch actuable to an "on" position for connecting said electrical energy supply means to said control means, further gate means responsive to turning on of said motor for establishing a shunt across said on/off switch for maintaining connection of said electrical energy supply means to said control means despite opening of said on/off switch, and time delay means responsive to turn off of said motor by said control means for timing a delay, means connecting said time delay means to said further gate means causing same to disconnect said shunt across said on/off switch upon termination of said time delay and in the absence of turning on of said motor during said time delay.

10. The apparatus of claim 1 in which said motor is an electric motor having a winding, electronic switch means connected in series with said winding to flow current therethrough from said electrical energy supply means;

speed control means for turning said electronic switch means on and off wherein the longer the electronic switch means in on, the more energy is applied to the motor and the higher the speed and load handling capacity of the motor is;

means responsive to current through said electronic switch means and winding and also responsive to the temperature of said electronic switch means for producing a representative voltage signal;

means responsive to a change in said voltage signal beyond a threshold, in response to at least one of winding current and electronic switch means temperature going past a limit, for reducing the amount of energy applied to said winding by said electronic switch means, such that motor efficiency, in mechanical power output per unit electrical power input, can be increased by reducing motor winding resistance without increasing the danger of motor winding burnout and electronic switch means burnout.

11. The apparatus of claim 10 in which said electronic switch means comprises a SENSFET having a high current drain connected to said winding and a low current drain, said voltage signal producing means comprising a voltage dropping resistance connecting said low current drain to a ground side of said electrical energy supply means, said resistance being connected to said means for reducing the amount of energy applied to said winding.

12. The apparatus of claim 10 in which said motor has three windings, said electronic switch means comprises three corresponding FETs, said FETs having gates arranged to be turned on in sequence and drains connected to said windings, Zener means connected to a nongrounded side of said electrical energy supply means, said drains being connected through respective diodes to said Zener means for bypassing high voltage spikes from said drains to recharge said electrical energy supply means.

* * * * *